Figure 1:
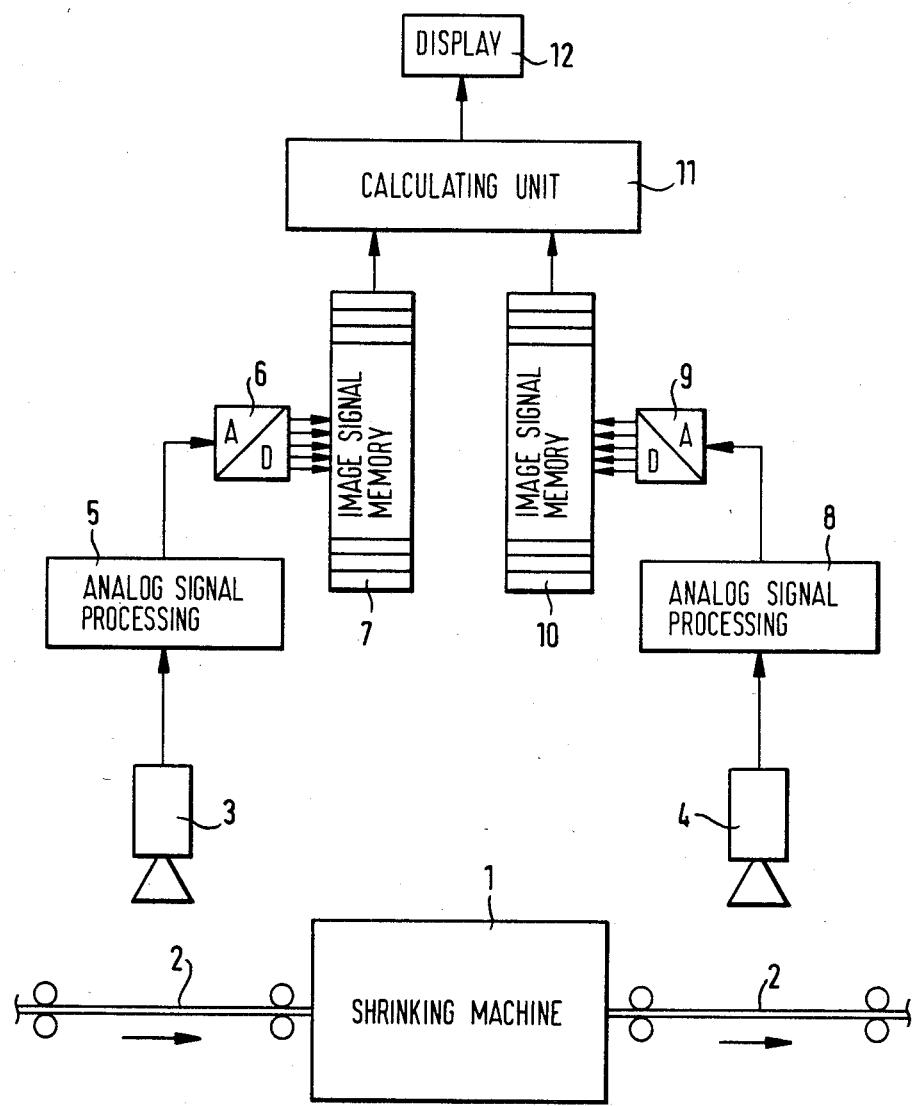

United States Patent [19]

Massen

[11] Patent Number: 4,586,372
[45] Date of Patent: May 6, 1986

[54] METHOD AND ARRANGEMENT FOR THE CONTINUOUS CONTACTLESS MEASUREMENT OF THE SHRINKAGE OF TEXTILES

[76] Inventor: Robert Massen, Kämpfenstrasse 39, 7760 Radolfzell 18, Fed. Rep. of Germany

[21] Appl. No.: 729,112

[22] Filed: Apr. 30, 1985

[30] Foreign Application Priority Data

May 8, 1984 [DE] Fed. Rep. of Germany ....... 3416883

[51] Int. Cl.$^4$ .......................................... G01N 33/34
[52] U.S. Cl. ........................................ 73/159; 26/51.5
[58] Field of Search ................... 73/159, 160; 364/470; 19/242; 26/51.5, 51, 51.4, 18.5, 19, 20, 21, 22, 23, 24

[56] References Cited

U.S. PATENT DOCUMENTS

| | | | |
|---|---|---|---|
| 3,554,656 | 1/1971 | Eicken | 26/51.5 |
| 3,591,294 | 7/1971 | Neil | 73/159 |
| 3,609,318 | 9/1971 | Anderson | 364/470 |
| 3,673,865 | 7/1972 | Michaelsen | 73/159 |
| 3,721,809 | 3/1973 | Strandberg, Jr. et al. | 26/18.5 |
| 3,729,635 | 4/1973 | Shottenfeld | 26/51.5 |
| 4,017,722 | 4/1977 | Swanson | 26/51.5 |
| 4,031,752 | 6/1977 | Sanders | 73/159 |
| 4,430,720 | 2/1984 | Aemmer | 73/160 |
| 4,476,717 | 10/1984 | Murphy | 73/159 |

FOREIGN PATENT DOCUMENTS 929827 2/1962 United Kingdom ................ 26/51.5

Primary Examiner—Robert I. Smith
Assistant Examiner—David R. Schuster
Attorney, Agent, or Firm—Gerald J. Ferguson, Jr.

[57] ABSTRACT

For the continuous contactless measurement of the shrinkage of textiles during the production process, the image of a portion of the textile surface is picked up both before and after the shrinkage and converted to analog electrical image signals by means of an image/-signal transducer. The analog image signals are digitized by analog-digital converters and stored in image signal memories. A calculating unit determines from the stored digital image signals the periods of the textile structure both before and after the shrinkage in at least one evaluation direction, preferably in the longitudinal direction and in the transverse direction of the textile web. The change of length of the textile material in each evaluation direction is calculated from the ratio of the two periods determined in this direction. The method is in particular suitable for the measurement of the two-dimensional shrinkage of knitted textiles during the manufacturing process.

30 Claims, 21 Drawing Figures

FIG. 3
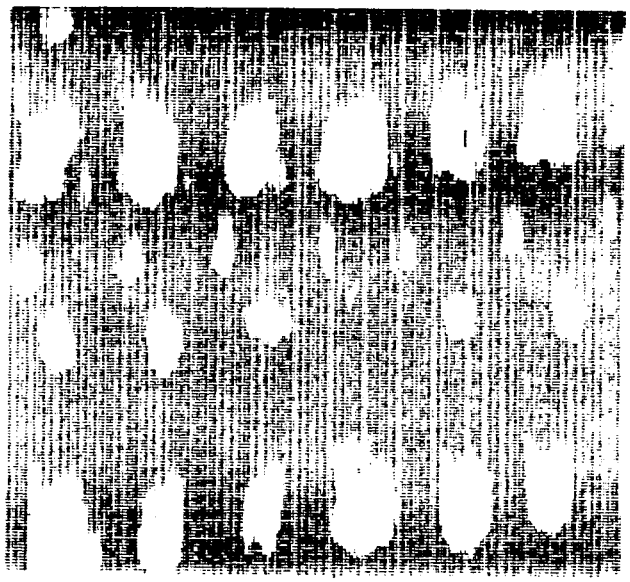
TRESHOLD : 30
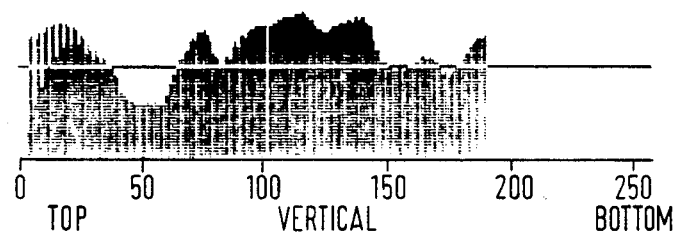
0      50      100      150      200      250
TOP            VERTICAL              BOTTOM
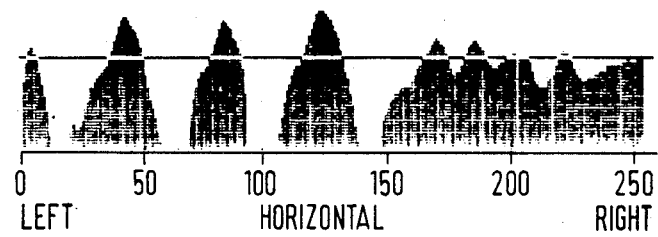
0      50      100      150      200      250
LEFT          HORIZONTAL             RIGHT

FIG.4
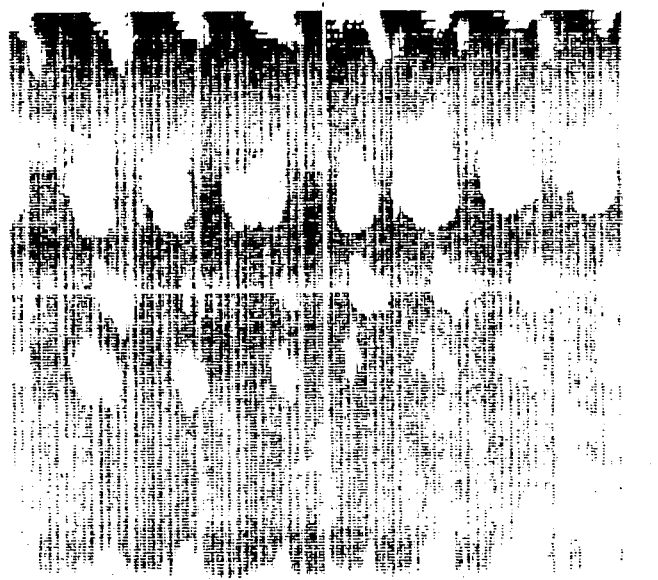
TRESHOLD : 29
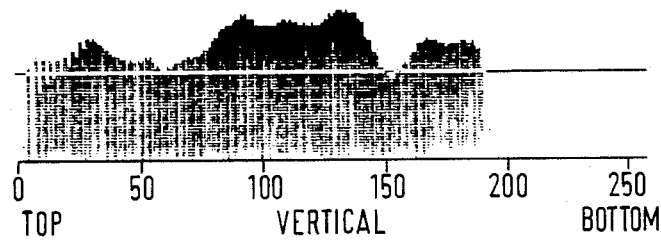
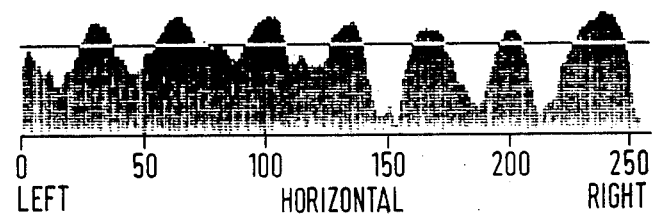

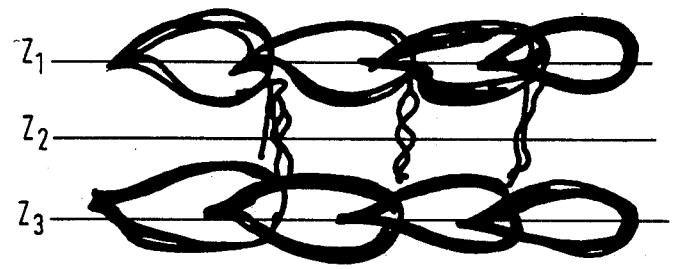
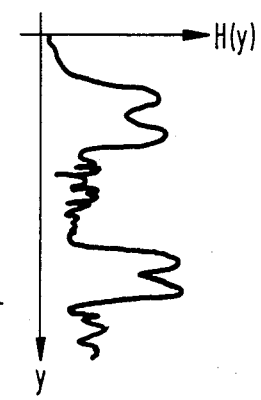
FIG.17    FIG.18
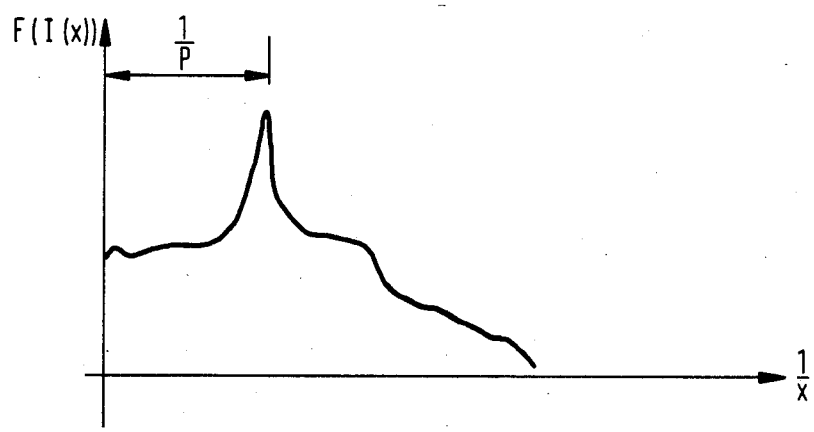
FIG.21

METHOD AND ARRANGEMENT FOR THE CONTINUOUS CONTACTLESS MEASUREMENT OF THE SHRINKAGE OF TEXTILES

The invention relates to a method for the continuous contactless measurement of the shrinkage of textiles during the production process and an arrangement for carrying out the method.

In weaving and knitting of yarns undesired potential energy is stored in the material. Subsequent washing and drying liberates this energy so that it is no longer available to maintain the shape: the material shrinks. Usually, a shortening in the longitudinal direction is accompanied by a widening in the transverse direction. Both processes are referred to as "shrinkage".

Manufacturers frequently subject the textiles made by them during production to a deliberate controlled shrinkage process to reduce subsequent undesirable changes in length. The material is thermally and mechanically processed in special shrinking machines to liberate again as much as possible of the potential energy introduced. To conduct this procedure exactly it would be necessary to determine by measuring methods the shrinkage obtained in real time and to do this as far as possible without contacting the frequently sensitive material. With textile webs of large length which are in continuous movement during the production process a direct measurement of the length change due to shrinkage is not possible without the (undesirable) application of marks. This applies in particular to the widely used circular knit fabrics which are produced in endless hoses. For this reason many manufacturers restrict themselves to measuring from time to time the change of the width of the textile web or the hose manually and on the basis of empirical relationships deducing the length shortening from the transverse extension. For several reasons this method is very unsatisfactory. The measurements contain many subjective errors and are discontinuous. Of the two-dimensional shrinkage process only the transverse extension is detected whereas the actually far more important shortening in length is determined only indirectly from the assumed constant relationship. Consequently, optimum and reliable execution of the shrinkage process is prevented by the lack of exact shrinkage data and this can also mean considerable economic losses.

The problem underlying the invention is to provide a method with which the shrinkage of textiles can be measured continuously with great accuracy during the production process, and an arrangement for carrying out the method.

To solve this problem the method according to the invention is characterized in that with the aid of an image/signal transducer the image of a portion of the textile surface is picked up both before and after the shrinkage and converted to analog electrical image signals, that the analog electrical image signals are digitized and stored in image point manner, that from the stored digital image signals the period of the textile structure in at least one direction before and after the shrinkage is derived, and that the change of length of the textile material effected by the shrinkage is calculated in each evaluation direction from the ratio of the two periods determined in this direction.

The method according to the invention utilizes the fact that knitted and woven textiles have a periodic structure whose period is influenced by a shrinkage process in the same manner as the dimensions of the textile material. In knitted fabrics the period is defined by the mesh structure and in woven fabrics by the intervals between the weft or warp threads. The ratio of the periods measured before and after the shrinkage in a given direction is therefore equal to the change of length in the same direction produced by the shrinkage.

With the method according to the invention the periods of the textile structure can be determined in any desired direction and even in several directions simultaneously. It is therefore in particular possible to measure at the same time a shortening in the longitudinal direction and a widening in the transverse direction. The measurement is carried out optically without any contacting of the textile material or intervention in the production process being necessary. The method is therefore particularly suitable for measuring the shrinkage of continuously moved textile webs or hoses. By suitable choice of the imaging scale with very different textiles in each case an image portion covering a few periods of the textile structure can be picked up, the image signals of which are suitable for determining the mean fundamental period or a multiple thereof. Of particular advantage is the fact that it is not necessary to measure the absolute magnitude of the period; only the ratio of the periods before and after the shrinkage is decisive.

There are several possibilities of deriving the period of the textile structure from the stored digital image signals. A suitable step is the formation of the unidimensional autocorrelation function of the digital image signals originating from an image point row lying in the desired evaluation direction. Instead of the autocorrelation function another related similarity function can also be formed. These and other further advantageous embodiments of the method according to the invention are explained in the following description and characterized in the subsidiary claims.

An arrangement for carrying out the method according to the invention contains according to the invention preferably an image/signal transducer which picks up the image of a portion of the textile surface before shrinkage and converts said image to an analog electrical image signal, an image/signal transducer which picks up the image of a portion of the textile surface after the shrinkage and converts said image to an analog electrical signal, an analog/digital converter following each image/signal transducer for digitizing the analog image signals, at least one image signal memory for storing the digital image signals furnished by the analog/digital converters and a calculating unit for deriving the period of the textile structure from the stored digital image signals.

Fundamentally, for the invention any image/signal transducer is suitable which can convert an optical image to analog electrical image signals which are suitable for a subsequent digitizing by image points. The best known example of such an image/signal transducer is a television camera which scans the picked-up image portion in a standard raster. For the purposes of the invention however such a television scanning is not necessary; matrix or line sensors as available commercially can also be used as image/signal transducer.

Figure 2:
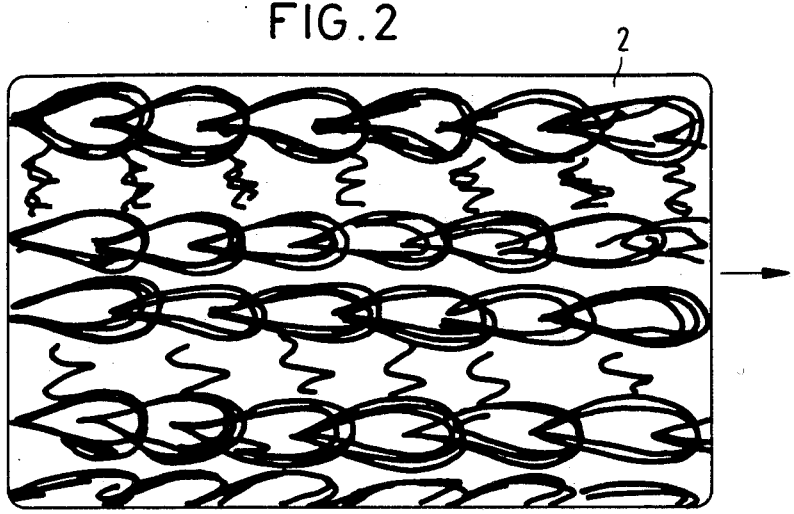
Figure 5:
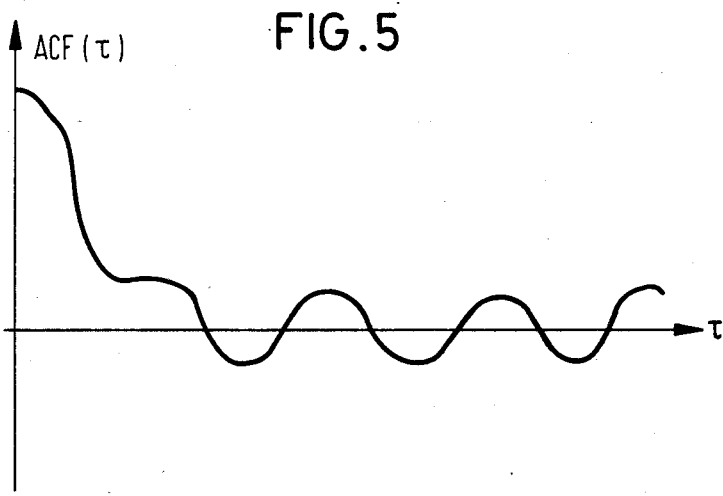
Figure 6:
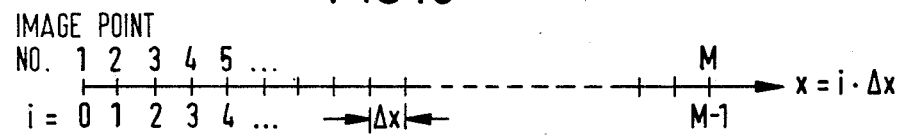
Figure 7:
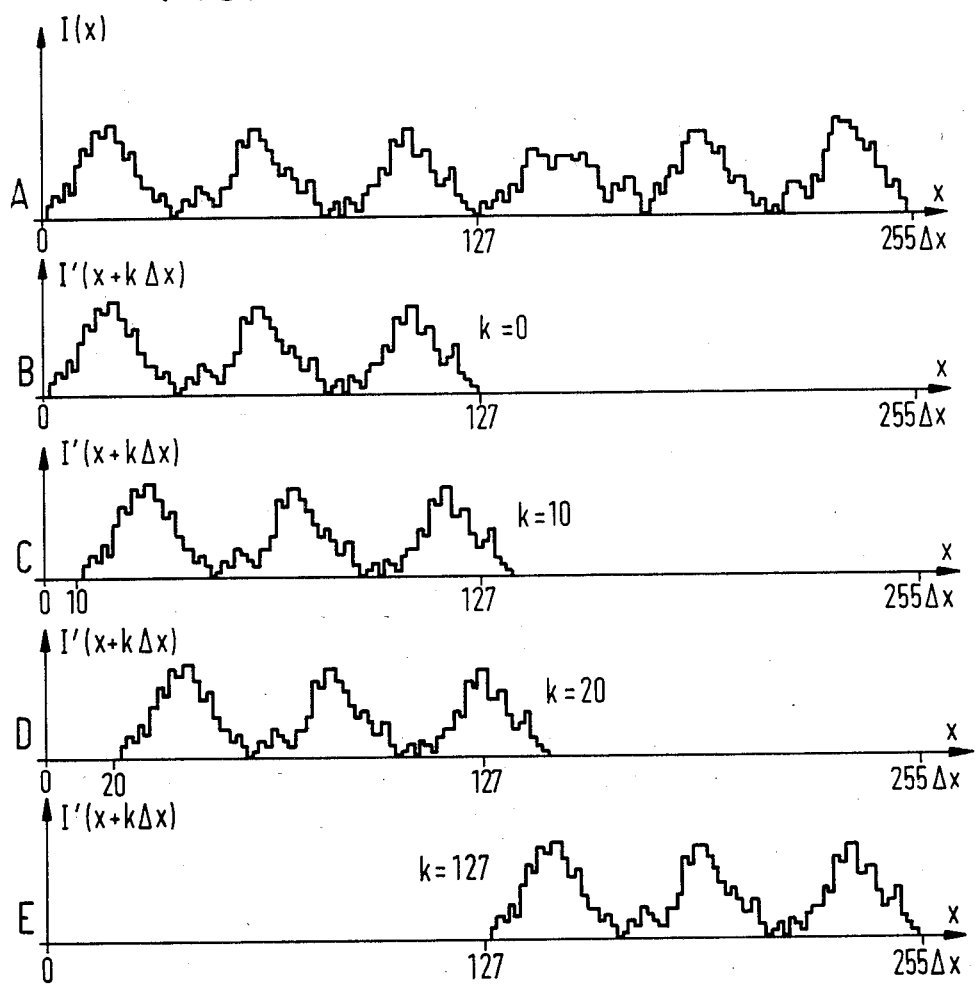
Figure 8:
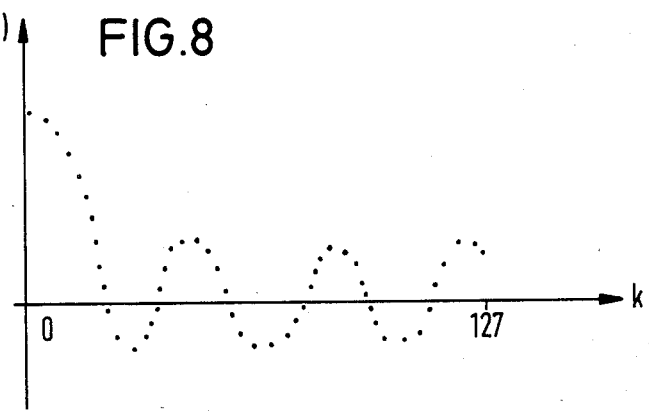
Figure 9:
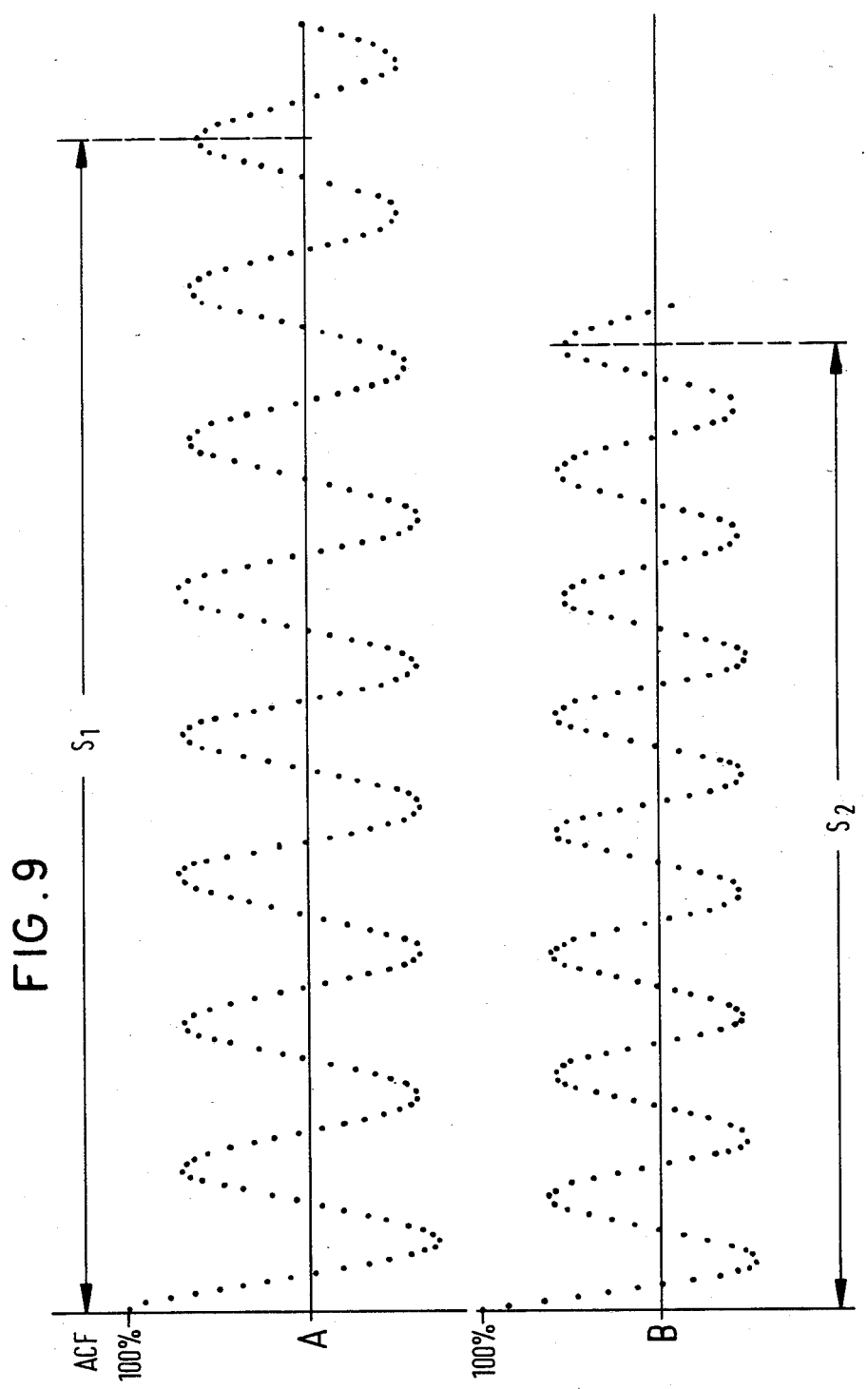
Figure 10:
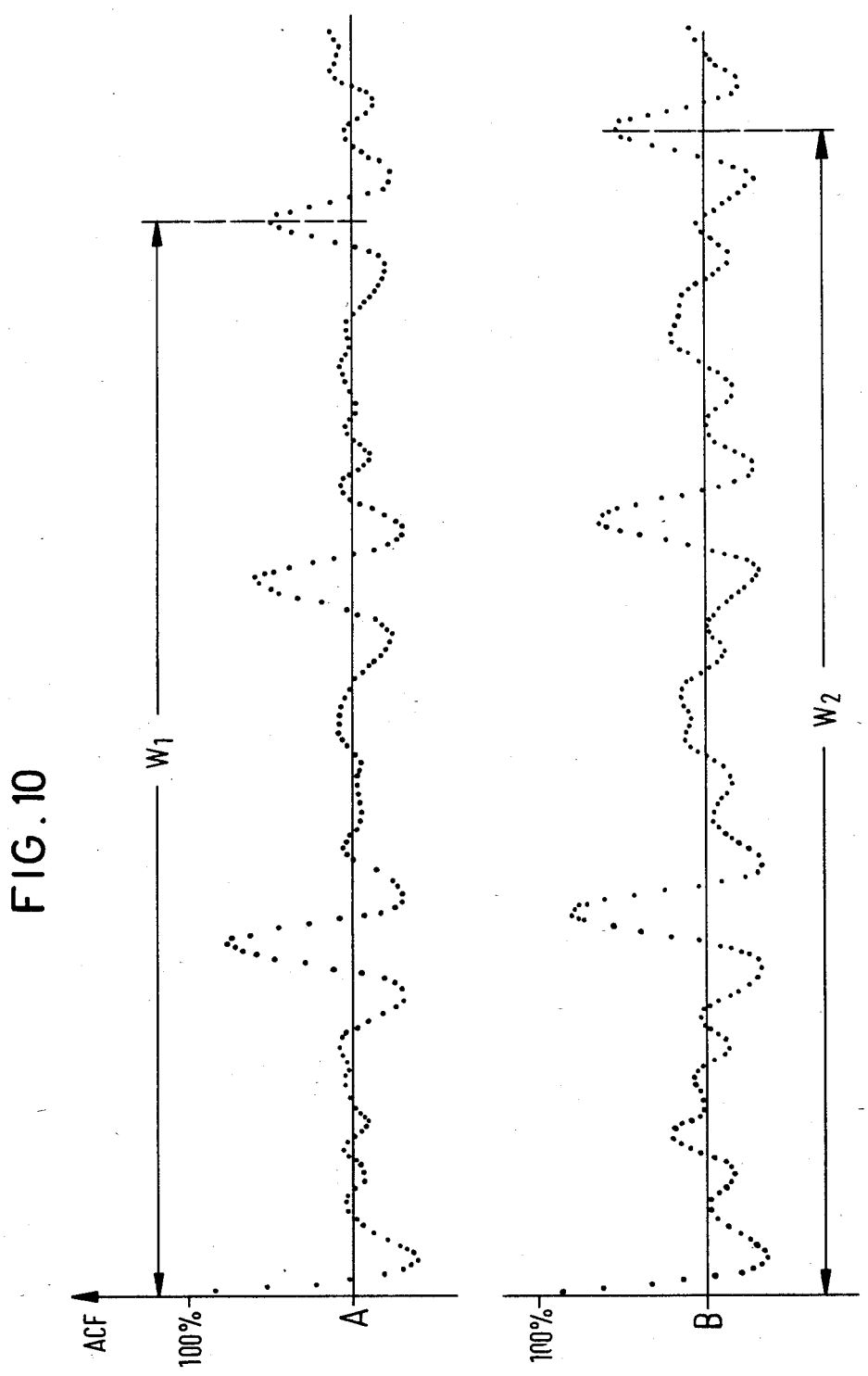
Figure 11:
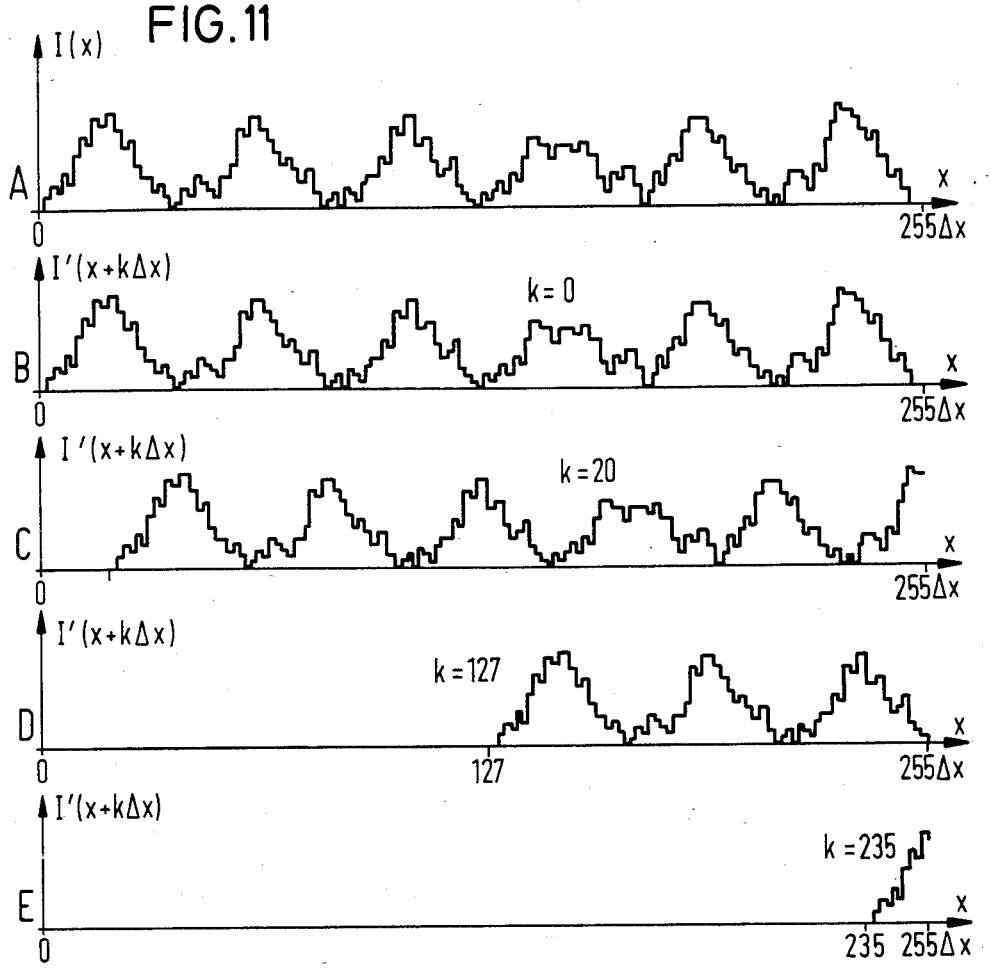
Figure 12:
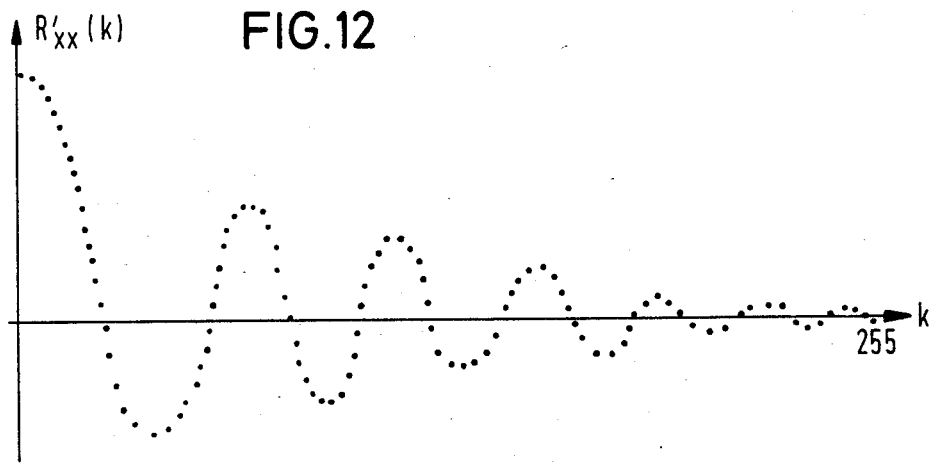
Figure 13:
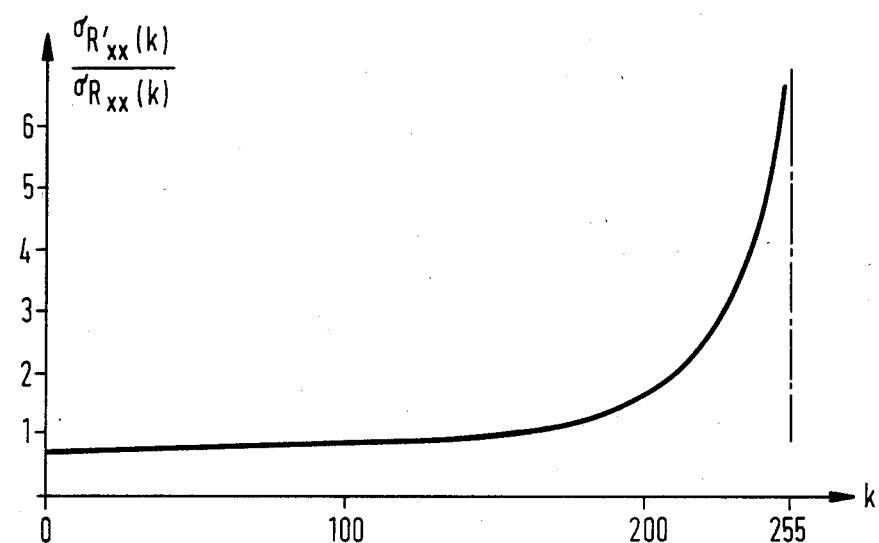
Figure 14:
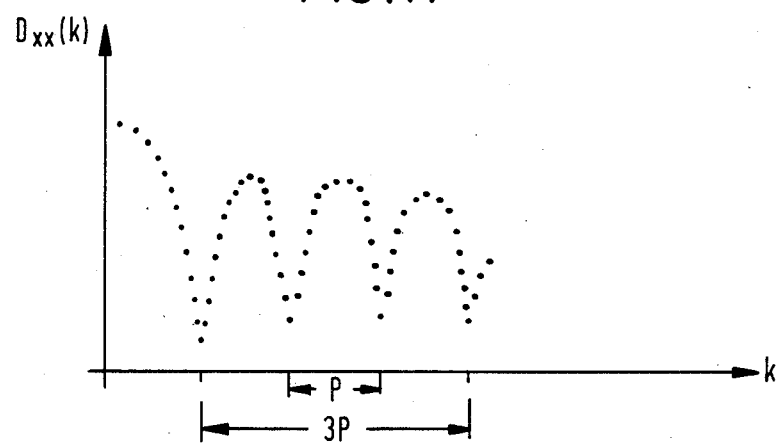
Figure 15:
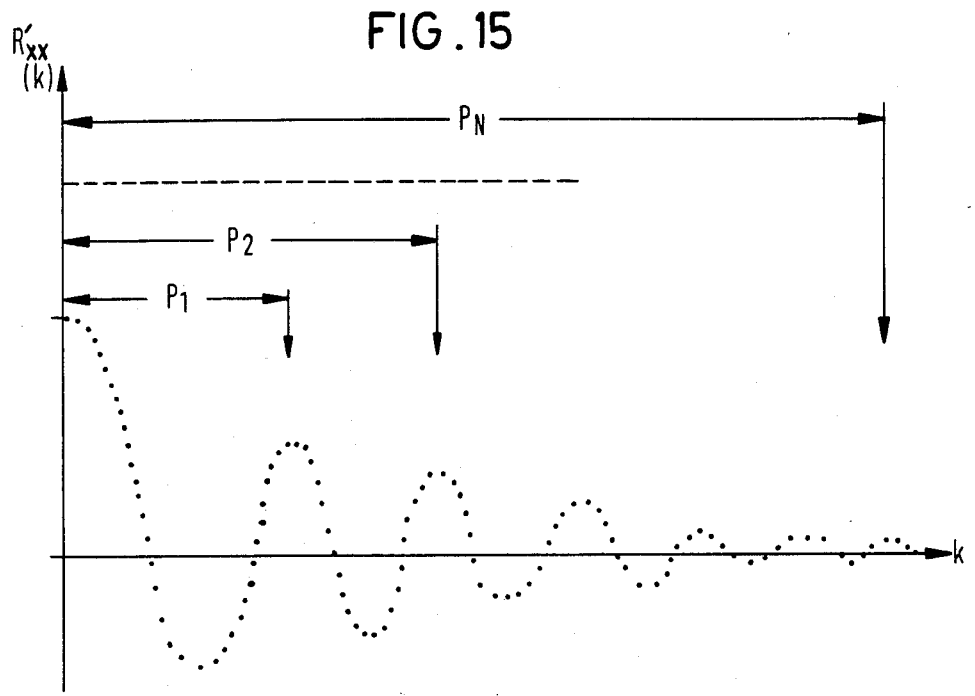
Figure 16:
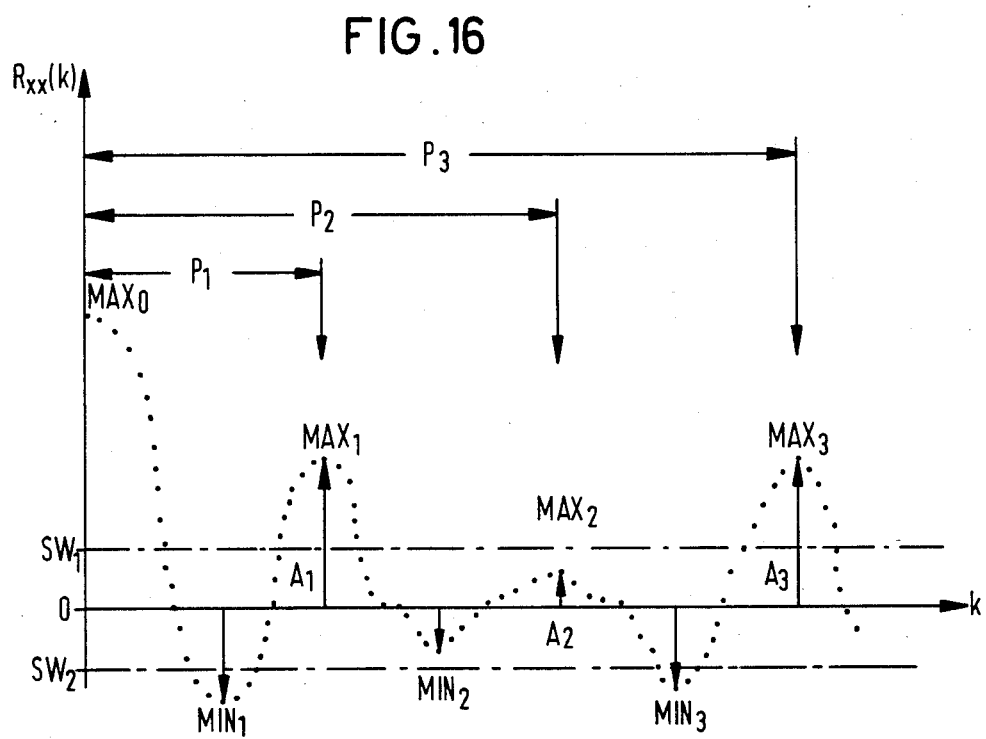
Figure 19:
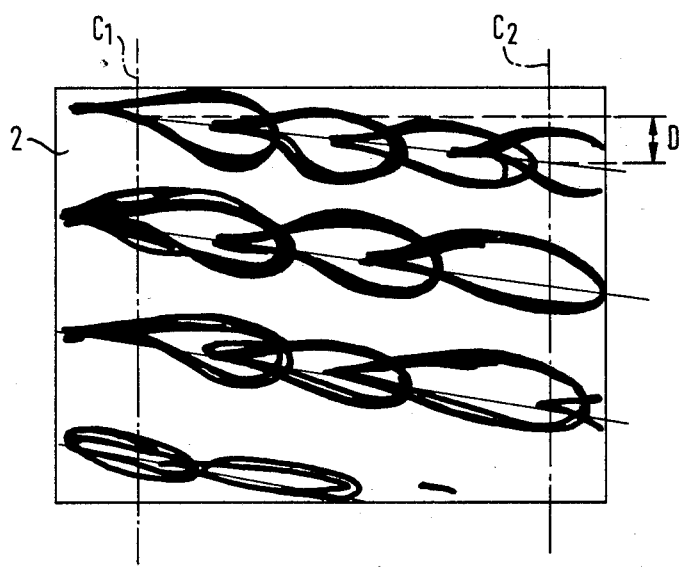
Figure 20:
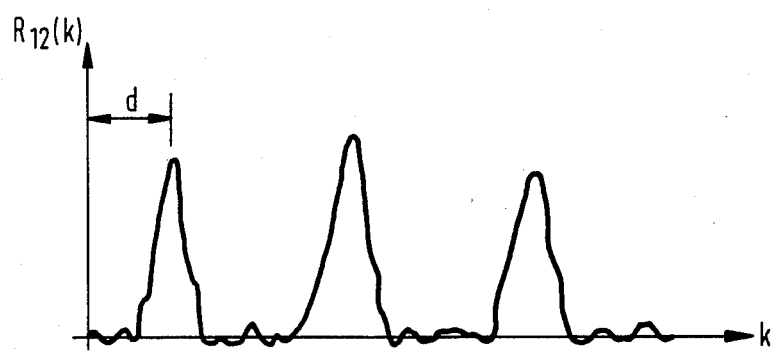

Further features and advantages of the invention will be apparent from the following description of examples of embodiment with the aid of the drawings, wherein:

FIG. 1 is a schematic diagram of an arrangement for measuring the shrinkage of a moving textile web, FIG. 2 is the stitch array of a knitted fabric forming the textile web, FIG. 3 shows the digital stitch image and the associated brightness profile in the transverse and longitudinal direction prior to shrinkage, FIG. 4 shows the digitized stitch image and the associated brightness profile in the transverse and longitudinal direction after the shrinkage, FIG. 5 is the autocorrelation function of a disturbed periodic signal, FIG. 6 is the schematic illustration of an image point row, FIG. 7 are diagrams explaining a method of forming the autocorrelation function from the digital image signals of an image point row, FIG. 8 shows the autocorrelation function obtained according to the method of FIG. 7, FIG. 9 shows autocorrelation functions obtained with a knitted fabric in the longitudinal direction before and after shrinkage, FIG. 10 shows the autocorrelation functions obtained with a knitted fabric in the transverse direction before and after shrinkage, FIG. 11 illustrates diagrams for explaining another method of forming the autocorrelation function from the digital image signals of an image point row, FIG. 12 shows the autocorrelation function obtained according to the method of FIG. 11, FIG. 13 is a diagram of the ratio of the dispersions of the measurement results obtained by the methods of FIGS. 7 and 11, FIG. 14 is the diagram of another similarity function suitable for determining the period, FIG. 15 is a diagram for explaining the obtaining of several periods from the autocorrelation function of FIG. 12, FIG. 16 is a diagram for explaining the evaluation of an autocorrelation function, FIG. 17 is the stitch image of a knitted fabric for explaining the selection of suitable image point rows, FIG. 18 is the brightness profile of the stitch image of FIG. 17 in the transverse direction, FIG. 19 is the stitch image of a knitted fabric with inclined stitch courses, FIG. 20 is a cross-correlation function formed to determine the inclination from the stitch image of FIG. 19 and FIG. 21 is the diagram of a spectral transformation of the stitch image suitable for determining the period of the textile structure.

FIG. 1 shows a shrinkage machine 1 through which a textile web is led in the direction of the arrow. The textile web 2 may be a woven fabric or a mesh fabric (knitted fabric). As example, in the following description it is assumed that the textile web 2 is a knitted fabric.

The textile web 2 is thermally and mechanically processed in the shrinkage machine 1 to produce a deliberate and controlled shrinkage which subsequently largely prevents undesirable changes of length by shrinkage. The degree of the shrinkage can be controlled by setting various influencing parameters at the shrinkage machine 1.

To carry out the shrinkage process exactly it is necessary to accurately measure the shrinkage reached by measurement techniques. For this purpose at the entrance of the shrinkage machine 1 a television camera 3 is disposed which picks up an image portion of the passing textile web 2 prior to entry in the shrinkage machine 1. At the output of the shrinkage machine 1 a second television camera 4 is disposed which picks up a similar image portion of the textile web 2 leaving the shrinkage machine 1.

Each television camera 3 and 4 is an image/signal transducer which converts the image portion picked up to an analog electrical video signal which is furnished at the output of the television camera. The analog video signal furnished by the television camera 3 is supplied after the necessary analog preparation in an analog signal processing circuit 5 to an analog-digital converter 6 in which it is digitized. The analog-digital converter 6 takes from the analog signal applied periodic sample values and converts each sample value to a digital signal. Each sample value corresponds to an image point (pixel) on a scanning line of the television image and its amplitude corresponds to the brightness value of the image point. In the analog-digital converter 6 the sampled amplitude value is quantized and converted for example to a binary code group which represents the brightness value in the form of a binary number. The position number of the binary number, i.e. the bit number of the code group, depends on the desired quantization resolution. In the simplest case a quantization with one bit can suffice, i.e. all brightness values lying beneath a predetermined threshold value are reproduced by the binary value "0" (black) and all brightness values above the threshold value are represented by the binary value "1" (white).

The digital output signals of the analog-digital converter 6 are input into a high-speed image signal memory 7 whose capacity is so dimensioned that it can store the digital signals originating from all image points of a complete scanning raster of the television camera 3.

In the same manner the analog video signal furnished by the television camera 4 is supplied after analog preparation in an analog signal processing circuit 8 to an analog-digital converter 9 in which it is digitized. The digital output signals of the analog-digital converter 9 are stored in a high-speed image signal memory 10. The circuit components 8, 9 and 10 have the same structure and the same mode of operation as the circuit components 5, 6 and 7 respectively.

Connected to the read outputs of the two image signal memories 7 and 10 is a calculating unit 11 which is for example a microcomputer. The calculating unit 11 can call up the digital image signals stored in the two image signal memories 7 and 10. It determines therefrom by a method still to be explained the shrinkage of the textile web 2 in the longitudinal direction and in the transverse direction. The relative shrinkage determined can for example be displayed by a digital display means 12 to enable an operator to adjust the shrinkage machine 1 accordingly. It is of course also possible to use the shrinkage values determined by the calculatinq unit 11 directly for controlling the shrinkage process.

FIG. 2 shows in schematic form the image portion of the textile web 2 picked up by a television camera when said web is a knitted fabric. FIG. 2 shows the stitch structure of the knitted fabric, the longitudinal direction of the knitted fabric corresponding to the direction of movement indicated by an arrow. The shrinkage of the knitted fabric is a global change of length process with shortening in the longitudinal direction and lengthening in the transverse direction. The geometrical changes are also detectable from the individual stitches.

FIG. 3 shows at the top a binarized stitch image, i.e. a real image converted by 1 bit quantization to black-white values, which has been picked up by a television camera before shrinkage and at the top of FIG. 4 the corresponding binarized stitch or mesh image after shrinkage is shown. The material is black and the mesh openings are shown in white. Beneath each binarized stitch image an associated brightness profile in the transverse direction (vertical) is shown and therebelow an associated brightness profile in the longitudinal direction (horizontal).

It is apparent from the binarized stitch images that the stitches and stitch openings vary greatly in form, size and spacing. It is therefore not possible to derive clear geometrical dimensions for assessing the shrinkage by evaluating a single stitch. The direct evaluation of the brightness profile does not permit this either because here too large individual fluctuations occur.

In the method carried out with the arrangement of FIG. 1 a different approach is adopted. The stitch image of FIG. 2 and the binarized stitch images of FIGS. 3 and 4 permit a certain periodicity of the imaged structure to be seen both in the longitudinal direction and in the transverse direction. The method used is based on the underlying idea of reproducing the knitted fabric as a greatly disturbed periodic process. If it is possible to isolate the fundamental period accurately enough from the noise changes of length can be represented directly as changes of this fundamental period.

The calculating unit 11 determines the noise-freed fundamental period both in the longitudinal direction and in the transverse direction prior to shrinkage and after shrinkage from the digital signals stored in the image signal memories 7 and 10 by using a suitable computation method. The digital signals stored in the image signal memory 7 give the two fundamental periods prior to shrinkage and the digital signals stored in the image signal memory 10 give the two fundamental periods after shrinkage. From the differences of the fundamental periods before and after shrinkage the relative shrinkage in the longitudinal direction and in the transverse direction is calculated.

A suitable method for determining the noise-free fundamental period is the formation of the unidimensional autocorrelation function of the image portion scanned by the television camera in the respective direction (longitudinal or transverse direction). As is known, the autocorrelation function (in short: ACF) is the correlation of a time function x(t) with the same time function $x(t-\tau)$ as a function of the time delay $\tau$. As FIG. 5 shows the autocorrelation function of a disturbed periodic signal consists of a component describing the superimposing of noise and period and a component which depends only on the period. To determine the fundamental period it therefore suffices to evaluate this second part. The fundamental period is derived from the interval between two successive maxima or with greater accuracy from the total interval of N consecutive maxima and division by N.

In the present case of television video signals the time function is defined by the brightness values of consecutive image points. To make this clearer in FIG. 6 the start and end of an image line is indicated, the continuous coordinate of the image line points being designated by x. The image points selected by the periodic sampling in the analog-digital converters 6 and 9 lie at uniform intervals $\Delta x$. The entire row includes M image points. If the first image point is referred to as image point No. 1 and has the coordinate $x=0$, the image point No. $(i+1)$ has the coordinate $i \cdot \Delta x$, and the image point No. M has the coordinate $(M-1) \cdot \Delta x$.

The autocorrelation function is defined by the sum of the pairwise products of the brightness values of image points of a line with the brightness values of image points of the same line displaced by k image points $$R_{xx}(k) = \sum_{i=0}^{L-1} I(i \cdot \Delta x) \cdot I((i + k) \cdot \Delta x) \quad (1)$$

with $k = 0, 1, 2, \ldots, (Q-1)$

Wherein:
$I(i \cdot \Delta x)$: is the brightness value (grey value) of the image point with the coordinate $i \cdot \Delta x$;
L: is the number of image point pairs processed for one value of the displacement operator k;
Q: is the number of calculated discrete values of the autocorrelation function.

For each value of the displacement operator k in accordance with equation (1) a discrete value of the autocorrelation function is obtained, i.e. a total of Q discrete values. For certain values of k the discrete values assume a maximum.

In diagram A of FIG. 7 the digitized brightness function $I(x)$ of an image line with $M=256$ image points as stored in one of the image signal memories 7, 10 of FIG. 1 is illustrated. To form the autocorrelation function the brightness function $I(x)$ is compared with an extract $I'(x+k \cdot \Delta x)$ of half its length which is displaced successively by $k=0, 1, 2, \ldots, 127$ image points. In the diagrams B, C, D and E of FIG. 7 the same extract $I'(x+k \cdot \Delta x)$ is illustrated after a displacement by $k=0$, $k=10$, $k=20$ and $k=127$. For each displacement each digitized brightness value of the extract $1'(x+k \cdot \Delta x)$ is multiplied with the brightness value vertically thereabove of the brightness funtion $I(x)$ of the diagram A. The number L of the image point pairs processed for each value of k according to the equation (1) is thus $L=M/2=128$.

To ensure that for all values of k there are still $L=M/2$ comparison pairs available Q must also be restricted to M/2. This results for example in an image line with $M=256$ image points in the autocorrelation function illustrated in the diagram of FIG. 8 with $Q=128$ discrete values. The autocorrelation function is not continuous but made up pointwise, each point corresponding to a discrete value. For certain values of k the discrete values have maxima because with the corresponding mutual displacement $k \cdot \Delta x$ due to the fundamental period of the structures compared maximum coincidence is obtained.

For the method explained with the aid of FIGS. 7 and 8 for forming the autocorrelation function equation (1) with the specified values $L=M/2$ and $Q=M/2$ reads:

$$R_{xx}(k) = \sum_{i=0}^{M/2-1} I(i \cdot \Delta x) \cdot I'((i + k) \cdot \Delta x) \quad (2)$$

with $k = 0, 1, 2, \ldots, (M/2 - 1)$.

The formation of the autocorrelation function is greatly facilitated in the arrangement of FIG. 1 by the storing of the digitized brightness values in the image signal memories 7, 10 because the calculating unit 11 can repeatedly read the data sets corresponding to the mutually offset line portions from the image signal memories.

To increase the statistical accuracy the autocorrelation function can be summed from a plurality of selected image lines. Technical television scanning systems with subsequent digitization and storing of the grey values frequently operate with 256 scanning lines.

The diagram A of FIG. 9 shows an autocorrelation function summed over eight scanning lines picked up from a knitted fabric before shrinkage, and in the diagram B of FIG. 9 the corresponding autocorrelation function of the knitted fabric is shown after shrinkage. The knitted fabric was so aligned that the line scanning direction of the television image corresponded to the longitudinal direction of the knitted fabric. The difference in the fundamental period between the unshrunk and the shrunk knitted fabric is clearly apparent and can be easily evaluated with the aid of the calculating unit. $S_1$ denotes the total period of eight stitches prior to shrinkage and $S_2$ the corresponding total period after shrinkage. The relative longitudinal shrinkage can then be calculated as:

$$S = \frac{S_1 - S_2}{S_1} \cdot 100\% \tag{3}$$

In the same manner the length changes in the transverse direction may also be determined. The image points vertically above each other in the television image are referred to as image column. The autocorrelation function of an image column is calculated in the same manner as the autocorrelation function of an image line, the displacement operator k corresponding to the line interval. The diagram A of FIG. 10 shows the autocorrelation function of the knitted fabric summed over eight parallel image columns in the transverse direction prior to shrinkage and diagram B of FIG. 9 shows the corresponding autocorrelation function after shrinkage. $W_1$ denotes the total period determined over three fundamental periods before shrinkage and $W_2$ the corresponding total period after shrinkage. As is apparent the period in the transverse direction prior to the shrinkage process is smaller than afterwards. The material undergoes a transverse widening and the relative transverse widening is calculated as $$W = \frac{W_2 - W_1}{W_2} \cdot 100\% \tag{4}$$

Thus, in both cases it is not necessary to determine the fundamental period itself; the shrinkage or widening desired can be derived directly from the total periods corresponding to a known multiple of the fundamental periods.

In many practical cases it is not necessary to detect the amplitude variation of the image point brightness because essential information is provided by the autocorrelation function even when only the signals quantized to one bit are correlated (polarity correlation function). This considerably simplifies the calculation because instead of products only Boolean combinations need be calculated. The measuring accuracy can be increased by high-pass filtering the analog video signal before the digitizing. By such filtering the high-frequency image structures, such as edges are emphasised and the correlation maxima intensified. The fundamental period can thereby be determined with better accuracy. In the arrangement of FIG. 1 the necessary high-pass filters are contained in the analog signal processing circuits 5 and 8.

Preferably, the television cameras are so aligned that the movement direction of the textile path extends parallel to the line scanning direction because this minimizes the movement blurring. With large feed speeds the textile web must be illuminated stroboscopically synchronously with the frame change. For this purpose an infrared flash is advantageously used and an infrared-sensitive semiconductor camera.

Since the shrinkage values in most practical cases vary only slowly the arrangement of FIG. 1 can be simplified by using instead of the two high-speed image signal memories 7 and 10 only one image signal memory into which the output signals of the analog-digital converters 6 and 9 are alternately entered.

FIGS. 11 and 12 show in similar form to FIGS. 7 and 8 a new method for forming the autocorrelation function. Diagram A of FIG. 11 again shows schematically the digitized brightness function I(x) of an image line with M = 256 image points and in diagrams B, C, D and E of FIG. 11 the extract I'(x+k·Δx) is shown which for various values of the displacement operator k is compared with the brightness function I(x) after a displacement through k=0, k=20, k=127 and k=235. The difference compared with the method explained with the aid of FIGS. 7 and 8 is that the extract I'(x+k·Δx) does not have a constant length of M/2 image points but includes in each case the entire remainder of the displaced image line overlapping the undisplaced image line. The comparison thus takes place with the displacement k=0 with M image point pairs and with increasing displacement k is made over a correspondingly decreasing number of L=M−k corresponding image point pairs. The displacement can take place theoretically up to the value k=M−1 so that Q=M discrete values of the autocorrelation function are obtained as illustrated in the diagram of FIG. 12. Equation (1) reads for this case:

$$R'_{xx}(k) = \sum_{i=0}^{M-k-1} I(i \cdot \Delta x) \cdot I'((i + k) \cdot \Delta x) \tag{5}$$

with $k = 0, 1, 2, \ldots, (M - 1); L = M - k; Q = M.$

Up to the displacement k=M/2 the products of more pairs are summed than with the method of FIG. 7 so that in this region a better statistical measurement accuracy is obtained. At higher values of k the measurement uncertainty increases which manifests itself in the diagram of FIG. 7 in the maxima becoming increasingly less pronounced.

In the method according to equation (2) explained with the aid of FIGS. 7 and 8 a maximum standard deviation $$\sigma_{R_{xx}}(k) = \frac{1}{\sqrt{M/2}} \neq f(k), \tag{6}$$

is obtained which is independent of the displacement k, whereas with the method explained with the aid of FIGS. 11 and 12 according to equation (5) the standard deviation is a function of the displacement k:

$$\sigma R'_{xx}(k) = \frac{1}{\sqrt{M-k}} = f(k) \qquad (7)$$

If the two dispersons are related to each other the result is $$\frac{\sigma R'_{xx}(k)}{\sigma R_{xx}(k)} = \frac{0.7}{\sqrt{1-k/M}} \qquad (8)$$

FIG. 13 shows this variation from which it is apparent that the statistical inaccuracy in the second method compared with the first method initially rises only very slowly with increasing displacement k. Thus, with a data set of M image points it is practically possible to calculate a similarity function of about 0.9·M discrete values by the second method without the discrete values additionally obtained compared with the first method being inadmissibly dispersed. Thus, the second method practically doubles the measuring range without the number of image points to be picked up and stored having to be increased.

Instead of the autocorrelation function other similarity functions can also be used to determine the mean fundamental period of the stitch or mesh image. Since to calculate the autocorrelation function products of the stored brightness values must be formed, a considerable expenditure of time and hardware is necessary. A similarity function which is simple to calculate is the sum of the quantity differences of the mutually displaced brightness values:

$$D_{xx}(k) = \sum_{i=0}^{L-1} |I(i \cdot \Delta x) - I((i+k) \cdot \Delta x)| \qquad (9)$$

with $k = 0, 1, 2, \ldots, (Q-1)$

The various letters have the meanings given previously for equation (1). The calculation can for example be made by the method of FIG. 7 with $L=M/2$ and $Q=M/2$ support values or also by the method of FIG. 11 with $L=M-k$ and a maximum of $Q=M$ support values.

The similarity function $D_{xx}(k)$ basically supplies the same information as the autocorrelation function $R_{xx}(k)$ but can be determined with far less expenditure. FIG. 14 shows the typical variation of the similarity function $D_{xx}(k)$ for a stitch image. The mean fundamental period P or the total period of several stitches preferably used for calculating the shrinkage can be determined most accurately from the periodic minima because these are sharper than the maxima.

Further suitable similarity functions which can be used for determining the period of the stitch image from the stored digitized brightness values are known in the literature.

An increase in the statistical measuring accuracy can be obtained by forming weighted mean values of a plurality of periods obtained from a similarity function. For example, with the autocorrelation function $R_{xx}'(k)$ obtained according to the method of FIGS. 11 and 12 and illustrated again in FIG. 15 the periods $P_1, P_2, \ldots, P_N$ of consecutive maxima measured from the origin can be linked as follows to give a mean total period $\bar{P}$:

$$\bar{P} = \frac{a_1 P_1 + a_2 P_2 + \ldots + a_N P_N}{a_1 + a_2 + \ldots + a_N} \qquad (10)$$

This gives a resolution which is greater than the quantizing step 1/M. The weighting factors are preferably so chosen that they run oppositely to the increase of the dispersion according to equation (8) so that measurement values with a greater dispersion enter the averaging less than values with a smaller dispersion.

A further improvement of the statistical measuring accuracy can be obtained in that the periods of a plurality of similarity functions are determined from a plurality of image rows of the same stitch image or of a plurality of successive stitch images and the similarity function is numerically smoothed and interpolated before the determination of the periods.

Due to greater irregularities in the stitch structure, for example due to considerable irregularities of the stitch values, because of creases in the textile web, etc., it may happen that in the periodic similarity function as well irregularities occur which can lead to errors in the determination of the fundamental period or the averaged total period. FIG. 16 shows as example an autocorrelation function $R_{xx}(k)$ having four successive maxima $MAX_0$, $MAX_1$ $MAX_2$, $MAX_3$, the maximum $MAX_2$ being only very weakly pronounced due to irregularities in the stitch image. To avoid errors, in the determination of the fundamental period or the mean fundamental period from the similarity function provision is made for using only portions which fulfil a certain quality criterion. Typically, such a criterion may be the amplitude. A maximum is only used for the evaluation when its amplitude exceeds a predetermined threshold value $SW_1$. If for example from the autocorrelation function $R_{xx}(k)$ of FIG. 16 the mean total period is calculated according to the above equation (10), the periods $P_1$ and $P_3$ defined by the maxima $MAX_1$ and $MAX_3$ are evaluated for the averaging because the amplitudes $A_1$ and $A_3$ of these maxima exceed the threshold value $SW_1$. On the other hand, the period $P_2$ defined by the maximum $MAX_2$ is not evaluated because the amplitude $A_2$ does not reach the threshold value $SW_1$ and therefore the maximum $MAX_2$ does not appear pronounced enough.

If the determination of the period of the stitch image is made on the basis of the minima in corresponding manner only minima are evaluated whose amplitude is below a predetermined threshold value $SW_2$. Thus, in the autocorrelation function $R_{xx}(k)$ of FIG. 16 only the minima $MIN_1$ and $MIN_3$ would be evaluated and not the minimum $MIN_2$. As explained above with reference to FIG. 14 evaluation of the minima is of particular interest when as similarity function the sum $D_{xx}(k)$ of the quantity differences is used.

To reduce the hardware expenditure and time requirement in calculating and evaluating the similarity function, it is advantageous to evaluate only image lines in which the stitch period occurs particularly clearly. These are in particular the image lines which extend centrally through the stitch holes because the similarity function calculated therefrom exhibits particularly pronounced maxima and minima. This might possibly make it unnecessary to carry out a further averaging. For example, with the stitch image of FIG. 17 the image lines $Z_1$ and $Z_3$ give particularly clear similarity functions whilst the image line $Z_2$, due to the weak contrast, can only supply very vague similarity functions. To determine the image lines best suited, the brightness profile H(y) transversely of the evaluation direction is formed as illustrated in FIG. 18 in spatial relationship to the stitch image of FIG. 17, and the image lines which have the most pronounced brightness differences in the profile wave form are evaluated. In the arrangement of FIG. 1 the formation of the brightness profile H(y) is effected by the calculating unit 11 on the basis of the image signals stored in the image signal memories 7 and 10. The calculating unit 11 evaluates the brightness profile H(y) and determines the addresses of the stored image signals which are to be used for calculating the similarity function. By this automatic selection of particularly pronounced image lines accurate measurement results can be obtained by evaluating only very few image lines.

Frequently, in practice an inclined running of the textile surface in the frame window of the television camera is inevitable because in particular with knitted fabrics a precise fabric guiding presents considerable technical difficulties. To nevertheless achieve an evaluatable unidimensional similarity function it is necessary to calculate said function along the inclination line of the stitch run. FIG. 19 shows as example the image portion of the textile web 2 picked up by a television camera with stitch rows running inclined to the line scanning direction.

The determination of the inclination can be made in that the cross-correlation function $R_{12}(k)$ or a corresponding similarity function is calculated between the image signals which are taken on the one hand from an image column $C_1$ at the left image edge and on the other from an image column $C_2$ at the right image edge. The cross-correlation function is defined by the sum of the pairwise products of the brightness values of image points of the one image column $C_1$ with the brightness values of image points of the other image column $C_2$ displaced by k image points; of course, in the column direction the image point interval $\Delta y$ is defined by the line interval or an integer multiple of the line interval. The cross-correlation function $R_{12}(k)$ is again calculated by the calculatinq unit 11 on the basis of the image signals stored in the respective image signal memories 7 and 10. Its variation is shown in FIG. 20. The distance d of the first maximum from the origin (with the conversion factor defined by the value $k \cdot \Delta y$) corresponds to the displacement D of the stitch centre line between the image columns $C_1$ and $C_2$. With the knowledge of the displacement D the calculating unit 11 can calculate the addresses of the stored image signals which originate from an image point row extending along the inclined stitch centre lines. As a result the measurement problem is again reduced to the calculation of a unidimensional similarity function. The evaluated image point row coincides in this case not with an image line but runs inclined over several image lines.

With pronounced inclination it may be expedient to form in the arithmetic unit 11 the two-dimensional autocorrelation function or a two-dimensional similarity function related thereto. The stitch period is then determined from the two-dimensional correlation profile obtained by the line of the most pronounced peak and valley sequences. The determination of two-dimensional correlation functions is prior art and need not be explained in detail here.

To the expert, numerous equivalent modifications of the method described and the arrangement set forth for carrying said method out will be apparent. Thus, in the above description it has been assumed that the image/signal transducers used for recovering the image signals are television cameras scanning linewise the image portion in a standard television raster. However, the method according to the invention is not restricted to the use of certain image/signal transducers. Instead of television cameras in particular standard-free matrix or line sensors may be used as are commercially available in various forms. Particularly well suited for example are CCD semiconductor matrix cameras with electronically variable integration time because their use possibly makes superfluous a stroboscopic illumination for avoiding movement blurring with moving textile webs.

The use of image/signal transducers other than television cameras is in particular also possible because it is not necessary to utilize the rapid frame repetition frequency of television cameras. On the one hand, the shrinkage changes only relatively slowly in the course of the production process so that it suffices to carry out the measurements at intervals which are large compared with the frame frequency of a television camera; on the other hand, the computation expenditure for determining and evaluating the similarity functions is so large that at the most it could be carried out within the frame period of a television camera only with very expensive high-speed computers. In a practical use of the method described above the measurements are carried out continuously at intervals of about 5 to 10 seconds. This suffices for calculating and evaluating the similarity function by a computer with a 32 bit microprocessor.

To reduce the influence of the colouring of the material to be investigated on the measurement result it is also possible to evaluate instead of the brightness structure the periodic height differences of the textile web. For this purpose, the surface of the textile web is illuminated at an angle of incidence which is so small that the periodic slight height differences of the stitches generate a corresponding periodic shadow pattern. This shadow pattern is independent of the colour of the textile material so that even completely black fabrics can be evaluated by the change from shadow and illuminated stitch peak.

Instead of from a similarity function the mean fundamental period of the stitch image can also be determined from the maximum of a spectral transformation of the stitch image. This can be done by using the Fourier transformation or orthogonal transformations related thereto, the Walsh transformation or the Hadamard transformation. Since for several of these transformations fast algorythms are known (e.g. the fast Fourier transformation algorythm), time can be saved by using them in particular in the calculation by microcomputers. In this case the stitch fundamental period is obtained from the dominant maxima of the spectrum as shown in FIG. 21 for the Fourier transformation result $F(I(x))$. Since the autocorrelation function and the Fourier transformation represent transformation pairs both contain the same information, although in a different representation.

I claim:

1. Method for the continuous contactless measurement of the shrinkage of textiles during production thereof, said method comprising the steps of:
    picking up an image of a portion of the textile surface both before and after the shrinkage with the aid of an image/signal transducer;

converting said image into analog electrical image signals;

digitizing said analog electrical image signals to give digital image signals;

storing said digital image signals image-pointwise;

deriving a first period of the textile structure in at least one evaluation direction before the shrinkage from the stored digital image signals;

deriving a second period of the textile structure in the same one or each evaluation direction after the shrinkage from the stored digital image signals; and calculating the change of length of the textile material caused by the shrinkage in the or each evaluation direction from the ratio of said first and second periods determined in this direction.

2. A method according to claim 1, wherein the periods of the textile structure are determined in two evaluation directions perpendicular to each other.

3. Method according to claim 2, wherein for measuring the shrinkage of a continuously moving textile web the periods of the textile structure in the longitudinal direction of the textile web corresponding to the direction of movement and in the transverse direction of the textile web lying perpendicular to the direction of movement are determined.

4. Method according to claim 1, wherein for deriving the periods of the textile structure a unidimensional similarity function of stored digital image signals is formed which originate from at least one image point row extending in the evaluation direction.

5. Method according to claim 4, wherein the unidimensional similarity function is the autocorrelation function.

6. Method according to claim 4, wherein the unidimensional similarity function is the sum of the quantity differences of the digital image signals of the mutually displaced image points of the same image point row.

7. Method according to claim 4, wherein for the formation of the unidimensional similarity function image point rows are evaluated in which the period structure is clearly apparent.

8. Method according to claim 7, wherein for selecting the evaluated image point rows the brightness function is formed along at least one image point row extending transversely of the evaluation direction.

9. Method according to claim 7, wherein for determining the direction of the image point rows to be evaluated for forming the unidimensional similarity function the cross-correlation function is formed between the image signals which originate from two image point rows extending transversely of the evaluation direction and spaced apart from each other.

10. Method according to claim 4, wherein to form the unidimensional similarity function the stored digital image signals of an image point row of M image points are compared with the stored digital image signals of an extract of M−k image points from the same image point row displaced continuously through k image points and the displacement k is increased beyond the value M/2.

11. Method according to claim 4, wherein only such portions of the similarity function which fulfill a predetermined quality criterion are evaluated for determining the period of the textile structure.

12. Method according to claim 11, wherein only maxima and/or minima of the similarity function which exceed or are below a predetermined threshold value are evaluated.

13. Method according to claim 4, wherein the period of the textile structure is derived by forming the means of a plurality of periods obtained from the same similarity function.

14. Method according to claim 13, wherein the periods obtained from the same similarity function are weighted to form the mean.

15. Method according to claim 4, wherein the similarity function is digitally smoothed prior to its evaluation.

16. Method according to claim 1, wherein for deriving the periods of the textile structure a two-dimensional similarity function of stored digital image signals is formed.

17. Method according to claim 1, wherein the periods of the textile structure are derived from a spectral transformation of the stitch image represented by the stored digital image signals.

18. Method according to claim 1, wherein the analog image signal furnished by the image/signal transducer is high-pass filtered prior to digitizing.

19. Method according to claim 1, wherein the analog image signal is binarized for digitizing by comparison with a threshold value.

20. Method according to claim 1, wherein the textile surface is illuminated synchronously with the frame change of the image/signal transducer in stroboscopic manner.

21. Method according to claim 1, wherein the textile surface is illuminated for generating showdows of the protuberances with light incident at the surface at a very small angle.

22. Arrangement for the continuous contactless measurement of the shrinkage of textiles during production thereof, said arrangement comprising:

an image/signal transducer for picking up an image of a portion of the textile surface before shrinkage and converting said image into an analog electrical image signal;

an image/signal transducer for picking up an image of a portion of the textile surface after the shrinkage and converting said image into an analog electrical image signal;

an analog/digital converter following each image/signal transducer for digitizing said analog image signals to produce digital image signals;

at least one image signal memory for storing said digital image signals furnished by said analog/digital converters; and a calculating unit for deriving the period of the textile structure from the stored digital image signals.

23. Arrangement according to claim 22, wherein each image/signal transducer is a television camera.

24. Arrangement according to claim 23, wherein for measuring the shrinkage of a continuously moving textile web the television camera is so aligned that the line scan direction runs parallel to the direction of movement of the textile web.

25. Arrangement according to claim 22, wherein each image/signal transducer is a matrix or line sensor.

26. Arrangement according to claim 25, wherein each image/signal transducer is a CCD semiconductor matrix camera.

27. Arrangement according to claim 22, wherein a stroboscope is provided which illuminates the textile surface synchronously with the frame frequency of the image/signal transducer.

28. Arrangement according to claim 27, wherein when using infrared-sensitive image/signal transducers the stroboscope is an infrared flash device.

29. Arrangement according to claim 22, wherein between each image/signal transducer and the associated analog/digital converter an analog signal processing circuit is provided.

30. Arrangement according to claim 29, wherein each analog signal processing circuit contains a high-pass filter.

* * * * *